US008394144B2

(12) United States Patent
Zehavi et al.

(10) Patent No.: US 8,394,144 B2
(45) Date of Patent: Mar. 12, 2013

(54) SYSTEM FOR POSITIONING OF SURGICAL INSERTS AND TOOLS

(75) Inventors: Eli Zehavi, Haifa (IL); Leonid Kleyman, Acco (IL); Eddie Batkilin, Nesher (IL)

(73) Assignee: Mazor Surgical Technologies Ltd., Caesarea (IL)

( * ) Notice: Subject to any disclaimer, the term of this patent is extended or adjusted under 35 U.S.C. 154(b) by 677 days.

(21) Appl. No.: 12/442,741

(22) PCT Filed: Sep. 25, 2007

(86) PCT No.: PCT/IL2007/001192
§ 371 (c)(1),
(2), (4) Date: Mar. 25, 2009

(87) PCT Pub. No.: WO2008/038282
PCT Pub. Date: Apr. 3, 2008

(65) Prior Publication Data
US 2010/0030232 A1    Feb. 4, 2010

Related U.S. Application Data

(60) Provisional application No. 60/846,749, filed on Sep. 25, 2006, provisional application No. 60/875,561, filed on Dec. 19, 2006.

(51) Int. Cl.
*A61F 2/44* (2006.01)
(52) U.S. Cl. .................................. 623/17.11; 606/130
(58) Field of Classification Search .............. 606/130, 606/99, 102, 96, 97, 86 R; 623/17.11–17.16; 600/407, 424, 425, 426
See application file for complete search history.

(56) References Cited

U.S. PATENT DOCUMENTS

| 6,725,080 | B2 * | 4/2004 | Melkent et al. ............... 600/424 |
| 6,837,892 | B2 | 1/2005 | Shoham |
| 2002/0077543 | A1 * | 6/2002 | Grzeszczuk et al. .......... 600/424 |
| 2006/0015030 | A1 * | 1/2006 | Poulin et al. ................... 600/424 |
| 2006/0084986 | A1 * | 4/2006 | Grinberg et al. ................ 606/61 |

FOREIGN PATENT DOCUMENTS

| WO | WO03/105659 | 12/2003 |
| WO | WO2005/032325 | 4/2005 |

OTHER PUBLICATIONS

PCT Int'l Search Report dated Mar. 23, 2009 and Written Opinion of the ISA, mailed Mar. 23, 2009 in PCT/IL2007/01192.
BrainLab AG of Feldkirchen, Germany re computer aided system for disc placement, Dec. 22, 2009. www.brainlab.com.

* cited by examiner

*Primary Examiner* — Eduardo C Robert
*Assistant Examiner* — Christina Negrellirodriguez
(74) *Attorney, Agent, or Firm* — Daniel J. Swirsky; AlphaPatent Associates Ltd.

(57) ABSTRACT

A tracking and positioning system and method to enable the precise positioning of an object or tool relative to its surgical surroundings, and in accordance with preoperative CT images of the operating site. When used for artificial spinal disc positioning, the system comprises a computing system incorporating in memory the preoperative CT data showing the two vertebrae and the predetermined disc position between them; a 3-D target having radio-opaque markers for attaching to one of the vertebrae to define the position of the vertebra in an intra-operative fluoroscope image of the spine; a tool for intra-operative insertion of the artificial disc, and a registration system for relating the intra-operative fluoroscope image to the preoperative CT data, such that the predetermined disc position is displayed in the fluoroscope image of the subject, thereby enabling the surgeon to place the artificial disc accurately in its intended position.

27 Claims, 8 Drawing Sheets

SYSTEM FOR POSITIONING OF SURGICAL INSERTS AND TOOLS

CROSS-REFERENCE TO RELATED APPLICATIONS

This application is a U.S. National Phase Application under 35 U.S.C. 371 of PCT International Application No. PCT/IL2007/001192, which has an international filing date of Sep. 25, 2007, and which claims priority from U.S. Provisional Patent Application Nos. 60/846,749, filed Sep. 25, 2006, and 60/875,561, filed Dec. 19, 2006, all of which disclosures are hereby incorporated by reference.

FIELD OF THE INVENTION

The present invention relates to the field of image reconstruction for ensuring the correct placement of surgical implants and tools, and especially to a system for ensuring correct surgical placement of artificial spinal discs.

BACKGROUND OF THE INVENTION

The use of artificial discs in spinal surgery to restore spinal mobility in patients with degenerative disc disease has been practiced for several years as an alternative to spinal fusion, and commercial systems for such disc replacement are available. The artificial discs are generally made of a hard plastic material which can pivot between two generally metal end plates attached to the adjacent vertebrae. One of the problems associated with this procedure is the need to insert the disc assembly into the correct position between the two adjacent vertebrae, such that it provides the correct pivoting action to the adjacent vertebrae. Since an advantage of disc replacement over spinal fusion is the maintenance of mobility, correct pivoting action is of great importance.

Figure 1A:
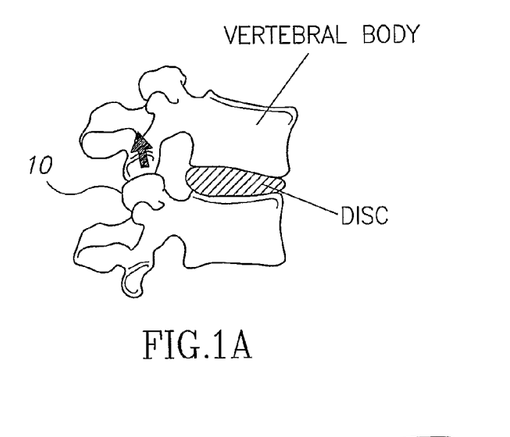
FIGS. 1A and 1B illustrate the facet joints of a pair of neighboring vertebrae, and the way in which they operate during spinal bending forwards and backwards.
Figure 1B:
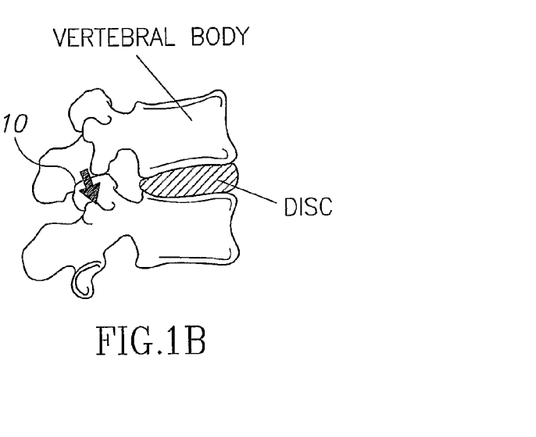

Located between and behind each pair of adjacent vertebrae, are the facet joints, which are small joints which stabilize the segments of the spine relative to each other, but nonetheless preserve the flexibility needed to turn, bend, twist and generally ensure spinal mobility. Reference is made to FIGS. 1A and 1B which illustrates these facet joints 10, and the way in which, during spinal bending forwards (FIG. 1A) and backwards (FIG. 1B), the facet joints are stressed in one direction or the other. The arrows show the direction of motion of the top facet for these two bending situations. If the artificial disc is not accurately positioned, the neighboring vertebrae will not maintain their correct mutual positions, and undesired forces may be applied to the facet joints, even when the patient is static. This situation becomes even more aggravating in motion, when the facet joints have to operate dynamically, and as the spine bends forwards or backwards, excessive tension or thrust is put on the facet joints, generating pain for the subject. In some cases, the pain limits subject mobility to such an extent that spinal fusion occurs naturally, and the spine loses its flexibility in that region. Malpositioning of the disc may lead to sliding of the disk from it original location due to excessive lateral forces acting thereon. This often requires surgical revision and in some cases can cause severe nerve damage.

The optimum disc position is generally taken to be laterally on the midline of the vertebral body, and, at least as recommended for use with the Charité™ Artificial Disc supplied by DePuy International Ltd. of Leeds, U.K., 2 mm dorsal to the sagittal vertebral midline. According to current practice, the disc positioning is performed by the orthopedic surgeon by observing the operating region in real time on a series of fluoroscope images taken at different angles, generally laterally and A-P. The surgeon estimates visually from the fluoroscope images when the disc is in the optimum recommended position. However, this procedure may be difficult to perform accurately since fluoroscope images may be difficult to interpret clearly because of the large mass of intervening soft tissue, and the desired midline positions cannot be clearly delineated from these images. Furthermore, this procedure involves a high radiation exposure, both to the patient, the surgeon and the O.R staff.

Recently, a computer aided system for disc placement has been described by BrainLAB AG of Feldkirchen, Germany, in which a navigation system is adapted for use in defining the position of the artificial disc in relation to the neighboring vertebrae. The optical navigator uses sources or optical reflectors positioned on the vertebrae themselves, and on the disc insertion tool in order to relate the position of the disc to the vertebrae themselves. This may well be an improvement over visual position estimating methods, but it involves a complex navigation system, and maintenance of clear lines of sight during the entire operation. Since anterior access is used for these procedures, this may not be a simple requirement to fulfill.

The placement of artificial Spinal replacement discs is only one of a large number of surgical procedures in which objects have to be accurately positioned within the body. Amongst such objects are various other orthopedic implants, and surgical tools which have to be accurately inserted into their destined location to perform their intended task. Like disc replacement, such procedures are often performed under minimally invasive conditions, where site visibility or access is limited, thereby placing heavy reliance on the experience and skill of the surgeon to ensure proper placement of the object or tool.

There therefore exists a need for a surgical positioning system which overcomes at least some of the disadvantages of prior art systems and methods.

The disclosures of each of the publications mentioned in this section and in other sections of the specification, are hereby incorporated by reference, each in its entirety.

SUMMARY OF THE INVENTION

The present invention seeks to provide a new tracking and positioning system and method to enable the precise positioning of an object or tool relative to its surgical surroundings, and in accordance with a preoperative plan of the surgical procedure, as generally prepared using pre-operative CT images of the operating site. The system is an Image Guided Surgery application which increases the accuracy of such procedures in comparison with methods previously used. The system and method are generally described in this application for use in the positioning of artificial disc inserts between the appropriate vertebrae of a subject, though it is to be understood that the procedure is not meant to be limited to this application but is applicable to any such suitable surgical insertion and positioning procedure.

The spinal disc positioning embodiment of the present invention uses a database of virtual implants, and allows preoperative planning of the surgical procedure, including implant positioning and spatial positioning and orientation of the surgical instrument holder or guide. Based on the preoperatively scanned CT data, the system generates a virtual model of the subject's spinal region where the operation is to be performed, and enables the determination of the optimum position of the disc on this model, this being the preoperative planning. During the replacement procedure, a registration process is performed between the preoperative CT data, and the real time fluoroscope images, so that the desired position of the disc, obtained from the preoperative CT scans, can be projected onto the real-life fluoroscope image. The surgeon can then position the real-life disc at the exact predefined position using this fluoroscope image.

The alignment procedure of the CT image with the real time fluoroscope images process cannot readily be performed using vertebrally attached registration plates, since such plates, unless mounted using a long holder that would then be prone to errors, would obstruct the surgeon's limited field of view and freedom of motion within the confines of the abdominal cavity where the operation is being performed. The system therefore preferably uses novel K-wires, or other types of surgical pins of similar function, having a special design with fiduciary markers such as spheres located on their shaft, and which are mounted on the vertebrae adjacent to the disc insertion site. According to one preferred embodiment, the special K-wires are registered with the conventional target plate early in the procedure, such that the target plate can then be removed and the tracking of the disc and associated vertebrae continued using the special K-wires, which do not impede the surgeon's view or actions.

According to a further preferred embodiment of the present invention, it is also possible to perform the registration procedure using only the novel K-wires but without using an additional target plate at all. In this embodiment, use is preferably made of at least two fiduciary balls on each of a pair of K-wires mounted in a vertebra in order to define the vertebra's position and orientation in three dimensions.

In the above described preferred embodiments, K-wires with fiduciary marker balls on their shafts are used in order to define the three-dimensional position of the vertebra. The use of spheres on the shaft ensures an accurate and simple registration process, since the center of a sphere has a well-defined and unique position. However, it is to be understood that the invention can also be implemented using regular K-wires, without any marker balls, and wherein the registration routine utilizes the alignment direction of the K-wires and their thickness in order to define the three-dimensional position of the vertebra in which the K-wires are stuck. This registration procedure may be more complex and possibly less accurate than that using defined marker balls on the shafts, but it does enable the use of standard components. In general, the invention is not intended to be limited by the means by which the registration is performed. Thus, for example, three K-wires in a vertebra, each with one marker ball can also be used.

Throughout this application, the various embodiments using K-wires are generally described in terms of the use of special K-wires having marker spheres, since this is generally the most accurate and simplest method to implement. However, wherever such special K-wires are mentioned, it is to be understood that this is not intended to be limiting, but is meant to include also other registration procedures using regular K-wires as mentioned hereinabove.

According to further preferred embodiments of the present invention, it is also possible to perform the disc insertion without removing the target plate, and hence without the use of any K-wire markers. This embodiment provides a simpler registration procedure, but can generally only be used where conditions are such that the target plate can remain in situ without disturbing the insertion procedure, and yet can still be used as a stable and accurate spatial reference.

According to a further preferred embodiment of the present invention, the optimum disc position is determined on the CT model by adjusting the disc position in the preoperative planning phase while viewing the spine kinematics and the effect of the disc position movement on the facet joints of the neighboring vertebrae. The optimum position and orientation is defined by that which places the facet joints under the least strain or compression, both with the spine static, and during motion.

According to a further preferred embodiment of the present invention, the disc insertion can be performed using a surgical robot. A particularly advantageous configuration is the use of a miniature surgical robot, which can preferably even be bone-mounted on a nearby part of the spine. In such cases, it may be advantageous, when a target plate is used, to leave the target in place during the robotic disc positioning, such that the target then has the multiple functions of being the co-ordinate reference frame for the fluoroscopic images, and for the robot guidance control. Alternatively and preferably, when marker balls on K-wires are used as the spatially defining targets, they can also be used as the spatial reference for relating the robot guidance control system to the vertebra location in the fluoroscope images.

According to the previously described embodiments, the registration procedure is used to relate the predetermined disc position onto the fluoroscope images so that the surgeon can position the disc over a virtual disc image implanted on the fluoroscope images. According to yet further preferred embodiments of the present invention, the registration procedure is performed as previously, with the optimum preoperatively defined disc position registered with the fluoroscope image data. However, according to this embodiment, this position is defined intraoperatively by aiming a physical pointer mounted in a known position relative to the vertebrae, at the correct point for the disc positioning in a fluoroscope image, so that the surgeon can then use the physical pointer to position the disc, without the need to look at more fluoroscope images. This method is preferably implemented by attaching an adjustable pointer to the K-wires, the pointer being adjusted manually after registration to point at the predefined disc location.

There is therefore provided in accordance with a preferred embodiment of the present invention, a system for intraoperatively placing an artificial disc at a predetermined position between two vertebrae of a subject, the system comprising:

(i) a computing system having a storage medium including a set of preoperative CT data showing the two vertebrae and the predetermined position of the disc between them, (ii) at least one target having radio-opaque markers adapted to be attached to at least one of the vertebrae to define the position of the vertebra in at least one intra-operative fluoroscope image of the subject, (iii) a tool for intra-operative insertion of the artificial disc, and (iv) a registration system for relating the at least one intra-operative fluoroscope image to the set of preoperative CT data, such that the predetermined disc position is displayed in the at least one fluoroscope image of the subject, thereby enabling intraoperative placement of the artificial disc in the predetermined disc position.

In the above mentioned system, the predetermined position of the disc is preferably obtained from predefined geometrical information about the position. This predetermined position of the disc may preferably be obtained by adjusting the disc position in a model obtained from the preoperative CT data, such that facet joints between the vertebrae are in minimally stressed positions. The at least one target is preferably a three dimensional radiographic target. Alternatively and preferably, the at least one target is at least two pins attached to each of the vertebrae, each of the pins comprising at least two radio-opaque markers disposed at known positions along the pins, such that the pins define the three dimensional position of the vertebrae in the fluoroscope images of the subject.

According to even another preferred embodiment, the at least one target is at least one pin attached to each of the vertebra, each of the pins comprising at least three radio-opaque markers disposed at known positions along the pins, such that the pins define the three dimensional position of the vertebrae in the fluoroscope images of the subject. In those embodiments using a target, the system preferably further comprises at least two pins attached to each of the vertebrae, each of the pins comprising at least two radio-opaque markers disposed at known positions along the pins, such that the pins define the three dimensional position of the vertebrae in the fluoroscope images of the subject, such that the target may be removed to allow intra-operative placement of the disc in the predetermined position. Furthermore, in those embodiments using a target, the system may alternatively preferably further comprise at least one pin attached to each of the vertebra, each of the pins comprising at least three radio-opaque markers disposed at fixed positions along the pins, such that the pins define the three dimensional position of the vertebrae in the fluoroscope images of the subject, such that the target may be removed to allow intra-operative placement of the disc in the predetermined position In any of the above described systems, the insertion tool may preferably be a manually operated tool or a robotically operated tool.

There is further provided in accordance with yet another preferred embodiment of the present invention, a method of intraoperatively positioning an artificial disc between two vertebrae of a subject, the method comprising the steps of:
(i) generating from a preoperative set of CT data, a CT model showing the vertebrae,
(ii) predetermining a position for the disc between the vertebrae, and defining the position in the model,
(iii) attaching at least one target to one of the vertebrae,
(iv) generating at least one fluoroscope image of the subject, such that the three dimensional position of the one of the vertebrae is defined in the at least one fluoroscope image by means of the at least one target,
(v) registering the at least one fluoroscope image of the subject with the CT model, such that a rendering of the disc in its predetermined position is shown on the at least one fluoroscope image, and
(vii) using the at least one fluoroscope image to position the disc intra-operatively such that it can be disposed in the predetermined disc position.

In the above described method, the artificial disc may preferably be disposed in the predetermined disc position by ensuring that the intra-operative position in the fluoroscope image essentially coincides with the display of the predetermined disc position. The predetermined disc position may be obtained either from predefined geometrical information about the optimum position, or by adjusting the disc position in the CT model such that facet joints between the vertebrae are in minimally stressed positions. The at least one target may preferably be a three dimensional radiographic target. The target may preferably be at least two pins attached to each of the vertebrae, each of the pins comprising at least two radio-opaque markers disposed at known positions along the pins, such that the pins define the three dimensional position of the vertebrae in the fluoroscope images of the subject. Alternatively and preferably, the at least one target may be at least one pin attached to each of the vertebrae, each of the pins comprising at least three radio-opaque markers disposed at fixed positions along the pins, such that the pins define the three dimensional position of the vertebrae in the fluoroscope images of the subject.

In accordance with still another preferred embodiment of the present invention, there is provided a method as described above, and further comprising the steps of:
(viii) providing at least four pins, each of the pins comprising at least two radio-opaque markers disposed at known positions along their length,
(ix) attaching at least two of the pins to each of the vertebrae, such that the pins define the three dimensional position of the vertebrae in the at least one fluoroscope image,
(x) utilizing the relationship between the known positions of the target and the pins to compute a transformation between the position of the target and the pins, and
(xi) removing the target to facilitate access to the vertebrae.

There is further provided in accordance with still another preferred embodiment of the present invention, a method as described above, and further comprising the steps of:
(viii) providing at least two pins, each of the pins comprising at least three radio-opaque markers disposed at known positions along the pins,
(ix) attaching at least one of the pins to each of the vertebrae, such that the pins define the three dimensional position of the vertebrae in the at least one fluoroscope image,
(x) utilizing the relationship between the known positions of the target and the pins to compute a transformation between the position of the target and the pins, and
(xi) removing the target to facilitate access to the vertebrae.

In accordance with a further preferred embodiment of the present invention, there is also provided a system for intraoperatively placing an artificial disc at a predetermined position between two vertebrae of a subject, the system comprising:
(i) a computing system having a storage medium including a set of preoperative CT data showing the two vertebrae and the predetermined position of the disc between them,
(ii) at least one target having radio-opaque markers adapted to be attached to at least one of the vertebrae to define the position of the vertebra in at least one intra-operative fluoroscope image of the subject,
(iii) a jig adapted to be attached to at least one of the vertebrae and supporting a reproducibly alignable pointer, and
(iv) a registration system for relating the at least one intra-operative fluoroscope image to the set of preoperative CT data, such that the predetermined disc position and the pointer are displayed in the at least one fluoroscope image of the subject, thereby enabling use of the pointer for intraoperative placement of the artificial disc in its predetermined position without the need to view a fluoroscope image.

There is provided in accordance with yet a further preferred embodiment of the present invention, a method of operatively positioning an artificial disc between two vertebrae of a subject, the method comprising the steps of:
(i) generating from a preoperative set of CT data, a CT model showing the vertebrae,
(ii) predetermining a position for the disc between the vertebrae and defining the position in the model,
(iii) attaching at least one target to one of the vertebrae,
(iv) generating at least one fluoroscope image of the subject, such that the three dimensional position of the one of the vertebrae is defined in the at least one fluoroscope image by means of the at least one target,
(v) registering the at least one fluoroscope image of the subject with the CT model, such that a rendering of the disc in its predetermined position is shown on the at least one fluoroscope image, (vi) attaching a jig to the vertebrae, the jig comprising a pointer which can be reproducibly aligned, (vii) viewing the pointer on at least one fluoroscope image and aligning the pointer such that it touches a predetermined part of the rendering of the disc, and (viii) using the pointer to position the disc intra-operatively, such that the disc can be disposed in the predetermined disc position without the need to view a fluoroscope image.

There is even further provided in accordance with a preferred embodiment of the present invention, a system for intraoperatively inserting a surgical tool into a predetermined position at a surgical site of a subject, the system comprising:

(i) a computing system having a storage medium including a set of preoperative CT data showing the surgical site and the predetermined position of the surgical tool, (ii) at least one target having radio-opaque markers adapted to be attached to a feature of the subject at the surgical site to define the position of the feature in at least one intra-operative fluoroscope image of the subject, and (iii) a system for registering the at least one intra-operative fluoroscope image to the set of preoperative CT data, such that the predetermined position of the surgical tool is displayed in at least one fluoroscope image of the subject, thereby enabling intraoperative insertion of the surgical tool into the predetermined position.

Furthermore, in accordance with yet another preferred embodiment of the present invention, there is provided a method of intraoperatively inserting a surgical tool into a predetermined position at a surgical site of a subject, the method comprising the steps of:

(i) generating from a preoperative set of CT data, a CT model showing the surgical site, (ii) predetermining a position for insertion of the surgical tool into the predetermined position at the surgical site, and defining the position in the model, (iii) attaching at least one target to a feature of the subject at the surgical site, (iv) generating at least one fluoroscope image of the feature such that the three dimensional position of the feature is defined in the at least one fluoroscope image by means of the at least one target, (v) registering the at least one fluoroscope image of the subject with the CT model, such that the predetermined position of the surgical tool is displayed on the at least one fluoroscope image, and (vi) using the at least one fluoroscope image to insert the surgical tool intra-operatively such that it can be disposed in the predetermined position.

BRIEF DESCRIPTION OF THE DRAWINGS

The present invention will be understood and appreciated more fully from the following detailed description, taken in conjunction with the drawings in which:

FIGS. 5 and 6 are fluoroscope images taken of the spinal region where the degenerated disc is being replaced, FIG. 5 being an AP image, while FIG. 6 is a 60° obliquely acquired LT image;

DETAILED DESCRIPTION OF PREFERRED EMBODIMENTS

Figure 2:
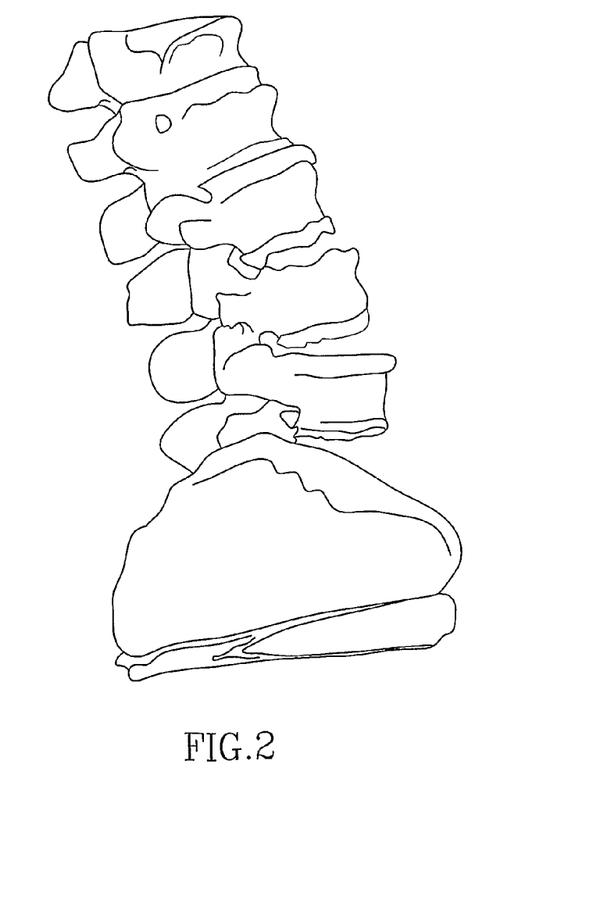
FIG. 2 illustrates schematically a model of the patient's spine, generated using data from preoperative CT scanning of the vertebrae.
Figure 3:
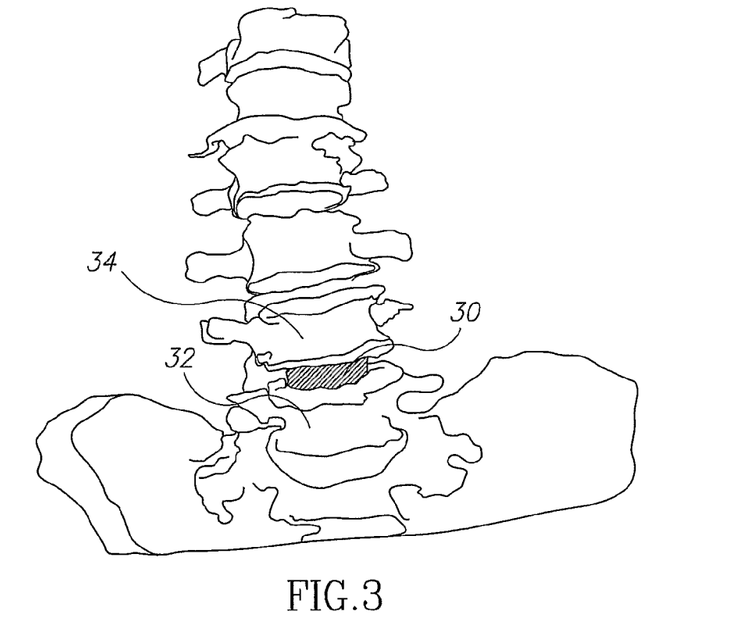
FIGS. 3 and 4 are respectively anterior and lateral views of the spinal model of FIG. 2.
Figure 4:
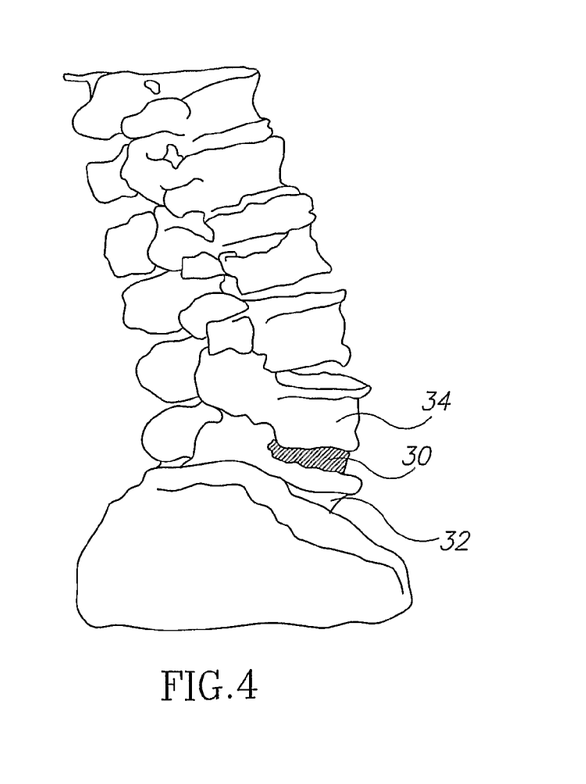

Reference is now made to FIG. 2, which illustrates schematically a model of the patient's spine, generated using data from preoperative CT scanning of the vertebrae. The model is built such that the separate vertebrae can be mutually virtually moved to enable insertion of the artificial disc between the desired vertebrae. The vertebrae are moved virtually by any of the generally available computer-based techniques, the most convenient being by use of the computer mouse, with the system software translating mouse movements to vertebral position movements. The vertebrae can be manipulated in all directions, both vertically, laterally and angularly, to enable correct insertion of the selected disc. The model takes into account the disc size and vertebral inclination. This is illustrated in FIGS. 3 and 4, which are respectively anterior and lateral views of the spinal model, showing how the artificial disc 30 is inserted virtually between the relevant adjacent vertebrae 32, 34.

The optimum AP position of the disc within the plane between the vertebrae must now be defined. This is done using the geometrical centers of rotation of the neighboring vertebrae. According to a currently widely accepted view, the preferred position is considered to be 2 mm dorsal to the sagittal vertebral midline, and laterally on the midline of the vertebral body. It is possible that this determination, though a good generally applicable rule of thumb, does not take into account individual features of the personal spinal anatomy of the patient being treated. According to a preferred embodiment of the present invention, the system enables the disc to be virtually maneuvered within its inter-vertebral space until the facet joints, as viewed on the virtual CT images of the model of the spine, are in the optimum bio-mechanical position, closest to their natural stance, as compared to that of the facet joints of neighboring vertebrae. This experimentally determined position takes into account any actual anatomical anomalies of the neighboring vertebrae to the new disc. This position should result in the minimum stress and loading of the facet joints, such that the success and the recovery rate of the procedure, as determined by recovered, pain-free mobility, should be optimized. This is in contrast to previously used procedures, where the standard location used for positioning the disc may not be the optimum for successful, pain-free motion recovery.

In practice, the correct disc configuration is chosen from a library of optional discs, according to the type, lateral size, angle and thickness required. The orientation, position and angle of the disc endplates is calculated, and, using a virtual representation of the disc size chosen, the disc endplates are placed on the operation plan by inserting the disk virtually into the spinal CT model. The vertebra can be moved apart and re-oriented in the model in order to obtain the correct positioning for the disc chosen, either according to a conventionally accepted standard position configuration, or by viewing the stress or distortion generated on the facet joints. The operation plan, showing the planned vertebrae orientation/ position is analyzed, preferably including the spine orientation during motion, and this then completes the creation of the preoperative plan, which is stored in the system for later intra-operative use.

Figure 5:
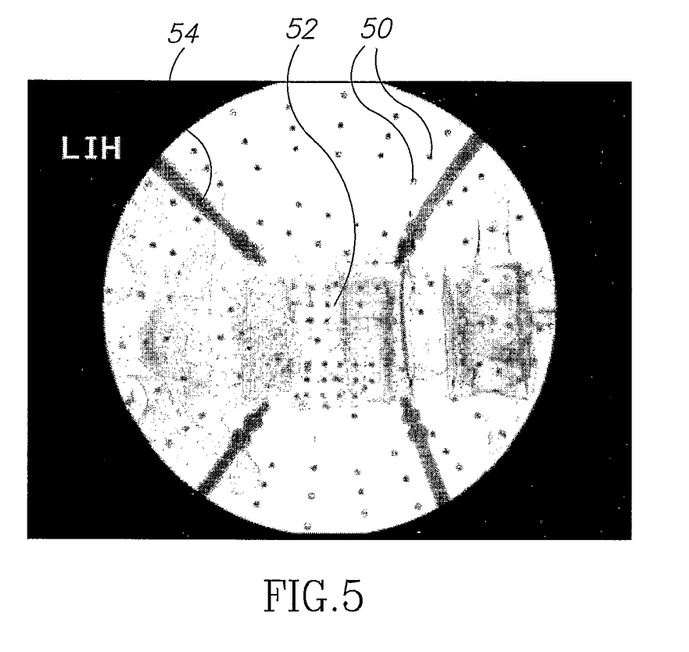
Figure 6:
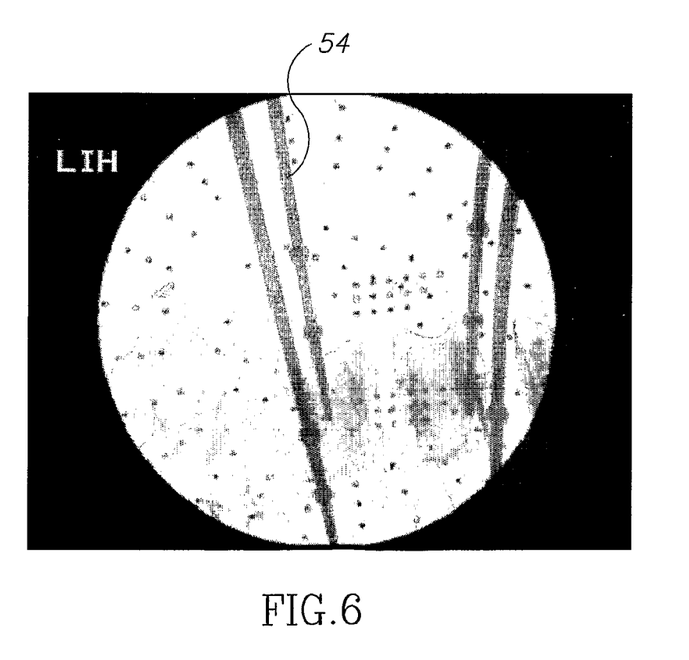
Figure 7:
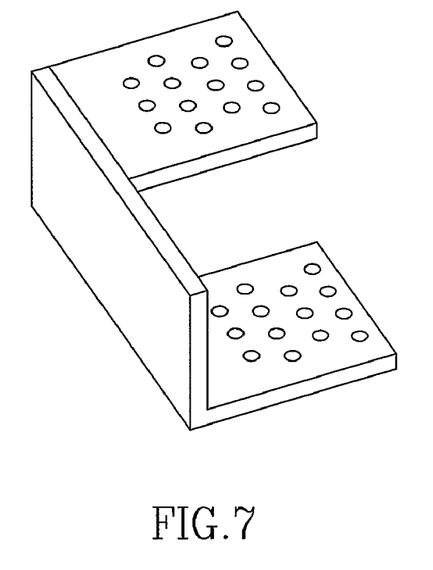
FIG. 7 is a schematic example of a 3-dimensional target plate for use in the registration process.

Hardware elements of the system are utilized during the operation itself. The procedure is first described using a removable target plate and K-wires for position determination. Reference is first made to FIGS. 5 and 6, which are fluoroscope images taken of the spinal region where the degenerated disc is being replaced. FIG. 5 is an AP image, while FIG. 6 is a 60° obliquely acquired image, though a lateral view could equally well be used. The outer set of fiduciary balls 50 seen in the images are from the conventional C-arm dewarping jig, used to calibrate the C-arm, as is known in the art. The closely spaced rectilinear array of balls 52 in the vicinity of the neighboring vertebrae is from a three dimensional registration target, used to define the co-ordinate system of the real time fluoroscope images. These fluoroscope images are first registered with the preoperative CT images on which the planning was performed, preferably by means of image processing procedures to match vertebral anatomic features between the two sets of images, as is known in the art. The preoperative CT images can thus be aligned with any real life fluoroscope image taken of the patient in real time during the surgical procedure, the fluoroscope image orientation and position being determined initially by means of the target. The target is preferably mounted on one of the vertebrae adjacent the disc to be replaced. Such a target can take a number of alternative forms, and preferably contains two separated planes of radio-opaque fiduciary marker balls, with a known geometric relationship between the two planes. A schematic example of such a target plate is shown in FIG. 7.

In each of FIGS. 5 and 6, four K-wires 54 can be seen, two inserted into each of the disc-adjacent vertebrae. K-wires, or equivalent devices such as Steinman pins, are conventionally used during anterior surgical exposure of the vertebrae, in order to retract the vasculature and soft tissues from the site of the disc. The K-wires of the embodiments of the system of the present invention shown in FIGS. 5 and 6 differ from conventional K-wires in that they have two spatially spaced balls on the lengths of the shafts, close to the insertion end. Knowledge of the distance between the positions of the balls on the shafts is not necessary, though it can be used to increase the accuracy of the registration process. Therefore, besides their above-mentioned use in the surgical procedure as simple pins, the K-wires of the present invention can be used to provide 3-dimensional positional data relating to the vertebrae. This function will be described below. Although the K-wires are shown with 2 fiduciary balls per wire, it is to be understood that a larger number of balls can be used per wire, such that the redundant data so provided enables a higher accuracy coordinate registration process. Alternatively and preferably, since the minimal number of spatial marker points required to define a three-dimensional co-ordinate system is three, it is possible to use a single pin in each vertebra, each pin having three spatial markers whose mutual positions are known. In this manner, not all of the ancillary surgical hardware required for use in the operation, such as the retracting pins mentioned above, need necessarily be associated with the marker function, since only one marker pin per vertebra is required. Additionally, as mentioned hereinabove, it is possible to use K-wires with less fiducial marker information, such a K-wires with only one ball, or K-wires without any marker balls, since the K-wire shape itself and its alignment can be used as fiducial marker information. The number of K-wires required per vertebra is determined according to the amount of fiducial data associated with each wire.

Since the vertebrae can move relative to each other, each vertebra whose position is important to the procedure, which generally means the two vertebrae either side of the replacement disc, requires its own set of K-wires to define its position in the fluoroscope images. In those surgical procedures where K-wires are not used, the operating table mounted retractors can be equipped with markers, and used for providing the spatially defined data for use in the registration processes. The assumption is made that there is no significant relative motion between the retractors and the vertebra, though this may limit the accuracy of a procedure using markered retractors.

The elements of the system of the present invention are utilized in this first preferred embodiment according to the following procedure. Using the target mounted on one of the vertebrae, the position and orientation (pose) of the X-ray imaging source relative to the target, and hence relative to the vertebra, is calculated, in the manner known in the art for such imaging systems. Once the source position is known, then from the imaged positions of the balls on the K-wires, the co-ordinate transformation between the target and the K-wires can be calculated. Once this transformation is known, then the target itself may be removed, and any further procedures can be carried out based on the now known positional information using the K-wire ball positions. The target is preferably removed, since the very limited space within the operation site would make it impossible to insert and manipulate the new disc if the target was in the way. The target could be held on an extension arm to avoid this problem, but this is less desirable since a long extension arm would add to the positional error. According to this first embodiment, the use of the special K-wires of the present invention therefore enables the real time fluoroscope images to be correlated with the preoperative CT scanned data, without the continued presence of a target plate during the surgical procedure.

According to a second preferred embodiments of the present invention, it is also possible to perform the disc insertion without removing the target plate, and hence without the use of the special K-wire markers, or special retractor markers. Where conditions are such that the target plate can remain in situ without disturbing the insertion procedure and the surgeon's field of view, and yet still provides a stable and accurate reference source, this embodiment enables the use of a simpler registration procedure.

According to a third preferred embodiment of the present invention, it is also possible to perform the disc insertion procedure without use of a target plate at all, by relying only on the special K-wire markers or special retractor markers to provide the data required regarding the position and orientation of the vertebrae. The K-wire positional data obtained from any fluoroscope image is used to determine any movement of the vertebrae between successive fluoroscope images. Comparison of this data then enables the position of any vertebra to be referenced back to the position of the first fluoroscope image, which itself was registered to the preoperative CT images, preferably by means of feature comparison, as explained hereinabove. Thus, any subsequent fluoroscope image can undergo co-ordinate transformation to the CT image co-ordinate system, such that the subsequent fluoroscope images can be displayed superimposed on the CT preoperative image, with the desired virtual disc position, as originally positioned on the virtual CT model of the spinal region of interest of FIGS. 3 and 4, but now shown on the real time, intraoperative fluoroscope image.

Figure 8:
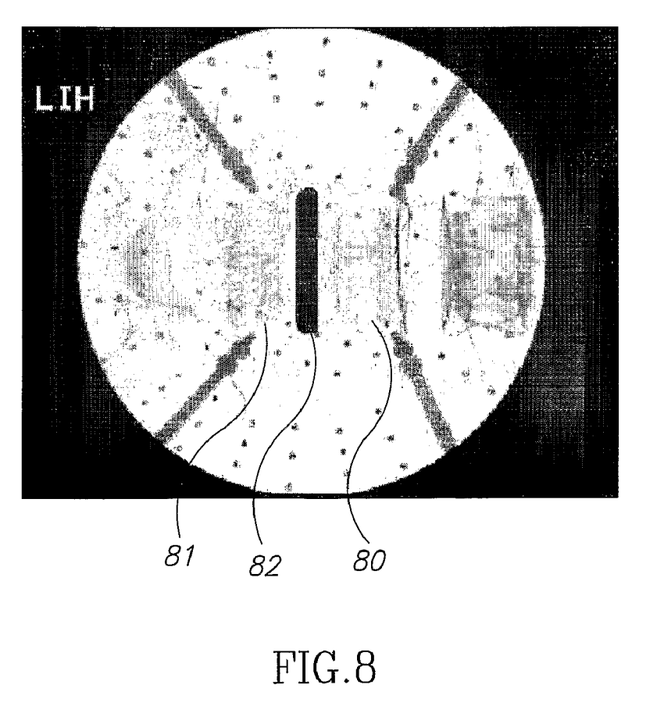
FIG. 8 is an AP fluoroscope image of the operation site, with a virtual image of the replacement disc implanted onto the real life fluoroscope image.

Reference is now made to FIG. 8, which is an AP fluoroscope image of the operation site, showing the two adjacent vertebrae 80, 81 between which the artificial disc 82 is to be inserted. Implanted onto the real life fluoroscope image is a virtual image of the desired disc, whose position is the optimized position, determined from the preoperative planning using the CT spinal model of FIGS. 3 and 4. This virtual disc then defines the optimum position of the real life disc which the surgeon has to insert, and is used as a guide for the surgeon as he manipulates the disc into place, until its fluoroscope image exactly covers the outline of the optimally positioned virtual disc from the CT scans. As a result of the preliminary registration procedure, regardless of which of the above mentioned procedures is used, the surgeon can view the real life images from differently oriented fluoroscope images, with the virtual disc displayed in the images in its planned intended position, such that he can position the disc correctly and accurately in both directions, fine tuning the final position by successive viewing of the disc positioning from different directions.

According to further preferred embodiments of the present invention, it is also possible to use a surgical robot to position the replacement disc into position. In this embodiment, the robot base plate is registered relative to the vertebrally fixed target, such as is described in U.S. Pat. No. 6,837,892, and in co-pending International Published Applications No. WO2003/105,659 and WO2005/032325, all hereby incorporated by reference, each in its entirety. The robot may be mounted either directly on one of the bones in the vicinity, or on the operating table adjacent to the patient, who then has to be immobilized. The transformation between the target plate and the special K-wires is then performed, such that the robot position is then known relative to the K-wires. The target plate may then be removed and the robot utilized to insert the disc using the appropriate tool, into a position determined preoperatively on the CT model, and now known to the spatial control system of the robot from the registration procedure. In such cases, and if appropriate from the specific surgical configuration, the K-wires can be dispensed with, and the target used throughout the procedure, including during the robotic disc positioning. The target then has the multiple functions of being the co-ordinate reference frame for the CT, for the fluoroscopic images and for the registration between them, for the virtual disc (as in fact already defined in the CT image), and for the robot guidance control. Alternatively and preferably, in those embodiments where a target plate is not used, and the registration is performed directly using the marked K-wires, the robotic placement is performed against the K-wire positions only.

Figure 9:
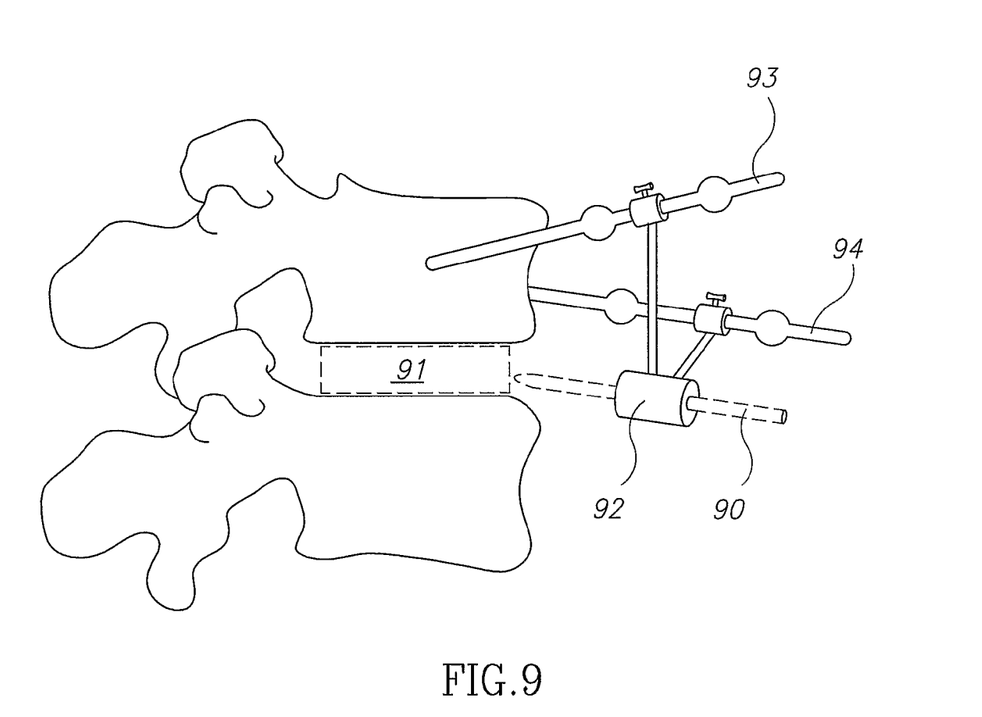
FIG. 9 is a schematic illustration of the use of a pointer attached to a K-wire, and, using the system of the present invention, aligned to the predetermined position in which the artificial disc is to be inserted.

Reference is now made to FIG. 9 which is a schematic illustration of the use of a pointer 90 attached in a known manner to the neighboring vertebrae, to assist the surgeon in positioning the artificial disc 91, according to further preferred methods of the present invention. In the illustration shown, the pointer 90 is carried in a sleeve 92 attached rigidly to two K-wires 93, 94 inserted into a neighboring vertebra. The pointer can preferably be adjusted within the sleeve to a predetermined position. As an alternative to use of such a sleeve and K-pins, any other suitable jigging arrangement which spatially defines the pointer position relative to the neighboring vertebra, can equally well be used in this embodiment. The system uses the same preoperative CT imaging and planning as in the previously described embodiments. As previously, the optimum predetermined position of the disc is implanted onto a fluoroscope image of the vertebrae of the subject after registration, and the surgeon then brings the pointer to a position between the vertebrae, such that its tip defines in real space, where a predetermined feature of the disc, such as the forward-most edge, is to be positioned. Once this relationship between the pointer and the optimum disc position has been established, no further fluoroscope images need be taken, thus significantly reducing the level of radiation used during the disc positioning procedure. The surgeon simply inserts the disc until it is located in the predetermined position relative to the tip of the pointer. Since the lateral position can often be accurately judged by the surgeon visually, the more critical positioning operation is the A-P position. In practical use, the pointer can be pre-aligned using the CT and first fluoroscopic image, so that its tip points, according to one preferred embodiment, to where the forward edge of the disc in its optimum position should be. The pointer is then withdrawn so that the disc can be inserted to close to its correct insertion depth, and the pointer reinserted in the sleeve to its predetermined position to see whether the disc is already in the correct position. This process can be repeated iteratively until the optimum position is achieved. Although the use of one pointer may provide sufficient accuracy to position the disc in both planar directions between the vertebra, more accuracy may be achieved using two such pointers, preferably with one defining the lateral position, and one the A-P position. By use of these methods of the present invention, the level of radiation used during the disc positioning procedure is significantly reduced.

Figure 10A:
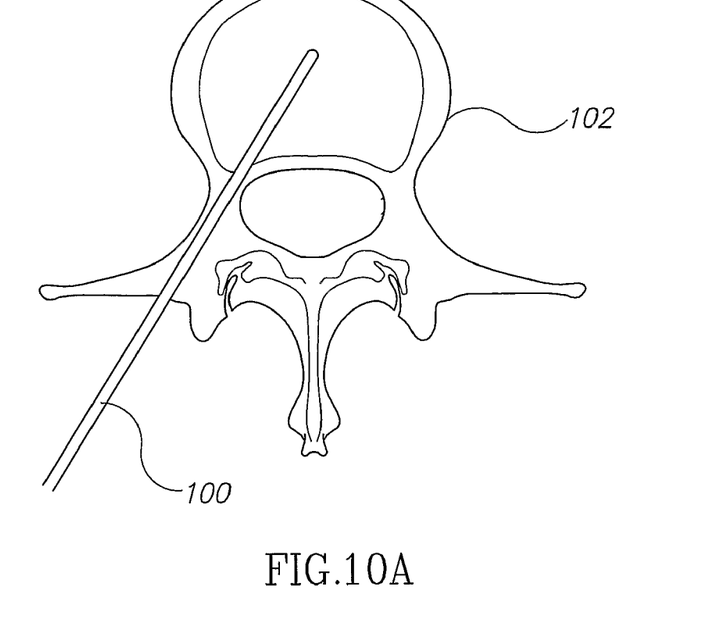
FIGS. 10A and 10B are schematic illustrations showing the positioning of a kyphoplasty needle in a subject's vertebra through the pedicle region, using the system and methods of the present invention.
Figure 10B:
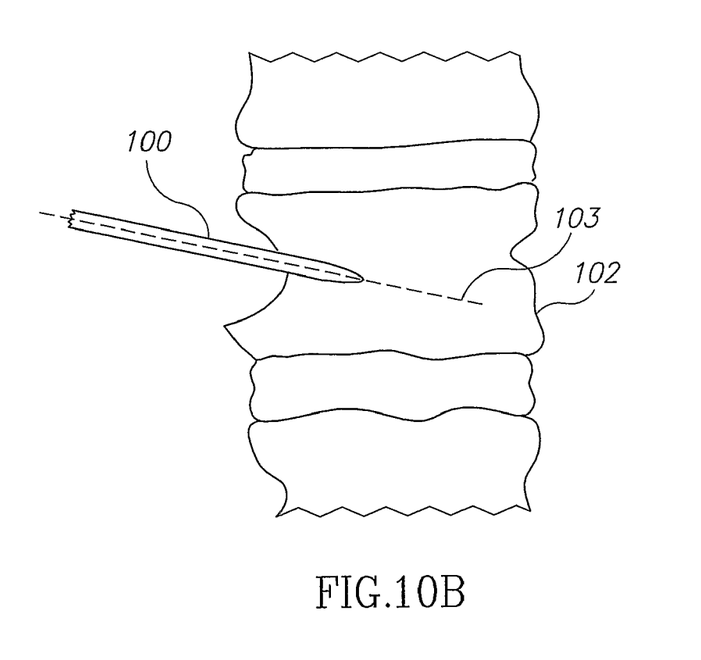

Reference is now made to FIGS. 10A and 10B which illustrate schematically how, according to a further preferred embodiment of the present invention, the system and methods of the present invention can be used for the accurate positioning of a kyphoplasty needle 100 inserted into a subject's vertebra 102 through the pedicle region. FIG. 10A shows a schematic axial CT image of a vertebra with a kyphoplasty needle inserted into the vertebral body from an extrapedicular direction. As is evident from the axial view, the surgeon requires great skill in order to ensure that the needle follows the desired path. Such an axial view is not generally available using a C-arm mounted fluoroscope system, and the surgeon must rely on AP or other laterally angled fluoroscope images for intra-operative guidance. FIG. 10B is a single oblique fluoroscopic image of the same procedure, showing the path of the needle into the vertebral body.

According to this preferred embodiment, the planned entry path of the needle is determined using preoperatively obtained CT images, and this optimum path is saved in the system memory. During the surgical procedure, a target with radio-opaque features is attached to the vertebra to be treated. As previously described, this target can be a conventional three-dimensional target plate, or one or more special marker attached K-wires inserted into the vertebra, or any other method which provides three dimensional definition of the position of the vertebra in the fluoroscope images. The fluoroscope images with the marker positions are registered to the preoperative CT image set, using image comparison as is known in the art, and a virtual image of the desired needle position and orientation can then be projected from the CT data, onto any fluoroscope image taken intra-operatively. As shown schematically in FIG. 10B, this desired path could preferably be marked as a dotted or colored line 103, so that it is clearly distinguishable from the image features. During the procedure, the surgeon can then view the progress of the needle insertion on the fluoroscope images, and can verify that the needle is following the desired path indicated on the fluoroscope image. In order to ensure correct adherence to the desired path, lateral and A-P images, or oblique images need to be viewed by the surgeon.

This procedure, according to the methods of the present invention, can be used for increasing the positioning accuracy for any surgical insert or tool which is amenable to the construction of a preoperative CT model of the surgical site and the definition thereon of the optimum position for the surgical insert or tool, and the registration of this CT model to intra-operatively generated fluoroscope images showing the actual progress of the insert or tool position, together with the pre-determined optimum position.

Figure 11:
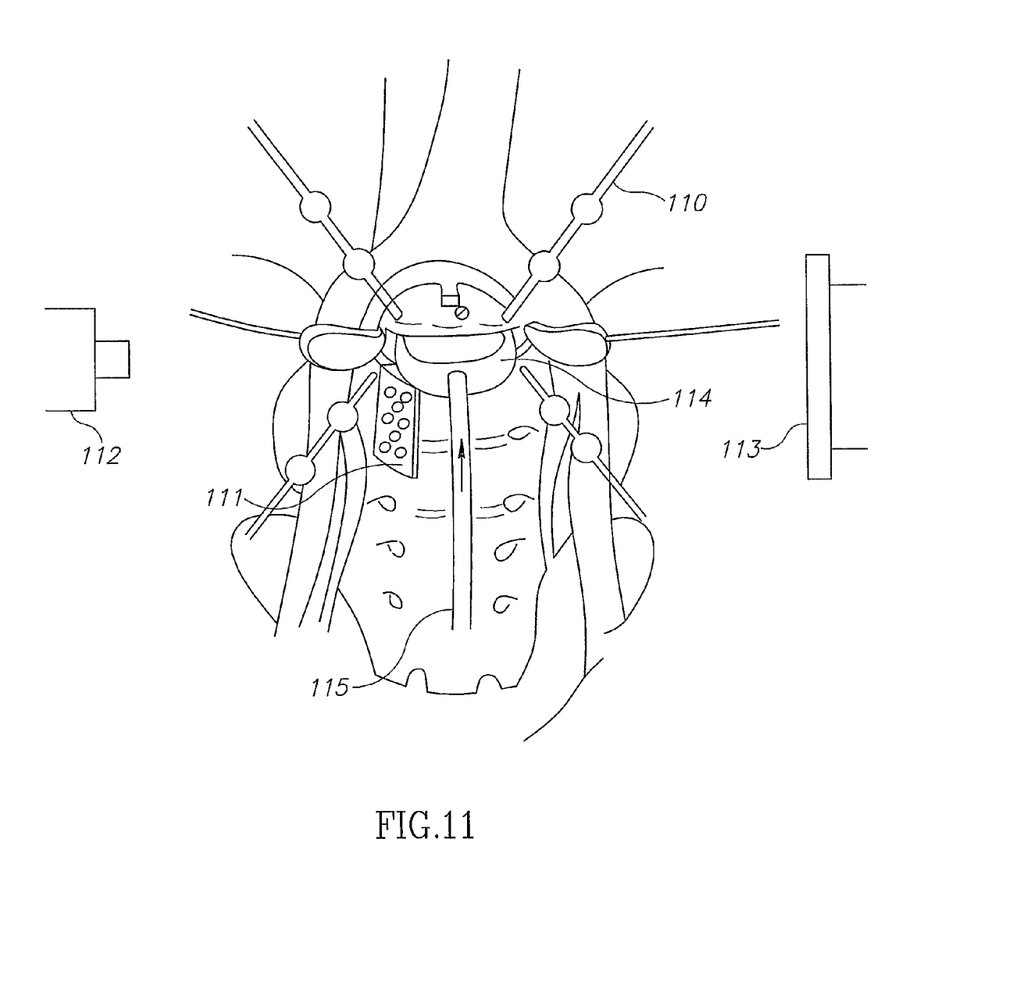
FIG. 11 illustrates the use of the hardware elements of the present invention in performing an artificial disc insertion into the L5-S1 disc space.

Reference is now made to FIG. 11, which illustrates the use of the hardware elements of the present invention in performing an artificial disc insertion into the L5-S1 disc space. The special K-wires of the present invention 110, with the marker balls on their shafts are shown inserted into the vertebrae, together with the three dimensional target 111, aligned such that it will be readily imaged in the fluoroscopic images of the region, which are taken using the schematically shown X-ray source 112 and camera 113. Once the registration to the special K-wire features has been performed, the target may be removed so that it does not impede the surgeon's view of the region. The target 111 in FIG. 11 is shown smaller than its preferable size, in order not to occlude details of the drawing. The artificial disc 114 is shown being inserted between the vertebrae using an insertion rod 115. The whole of the process is viewed on the fluoroscope images generated by the X-ray C-arm source and camera.

According to further preferred embodiments, the disc could be guided into position by means of a surgical robot, whose control system coordinates are registered to those of the preoperative CT scans, such that the robot can guide the disc into a predetermined position without any, or with minimal surgeon intervention. The robot could be either floor or bed mounted, or bone mounted, as is known in the art.

Figure 12:
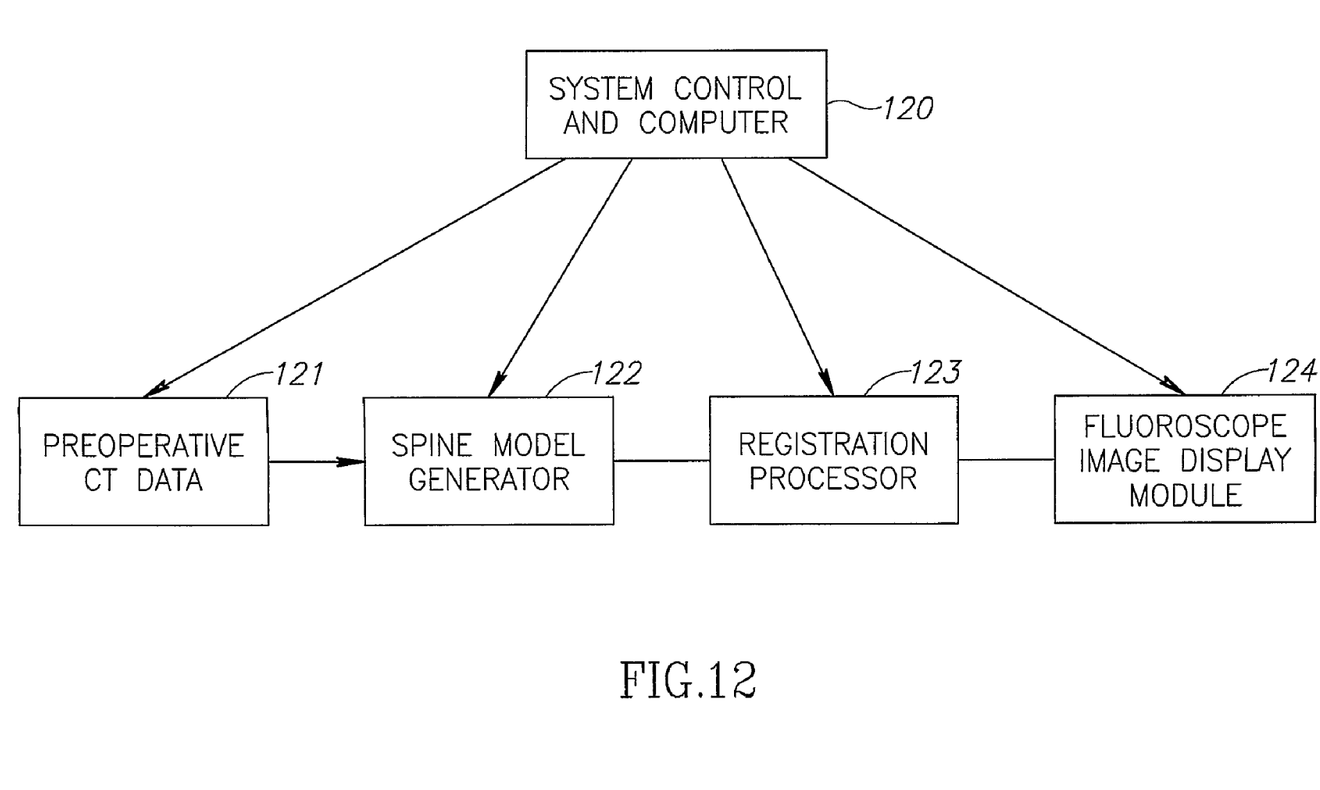
FIG. 12 illustrates schematically the control and computing elements of the system of the present invention, according to one preferred embodiment.

Reference is now made to FIG. 12, which illustrates schematically the control and computing elements of the system of the present invention. The preoperative CT data is stored in a storage medium 121, from where it can be transferred to the spine model generator 122 for building the virtual spinal model for use in planning the disc insertion position. Once the disc position has been determined, the registration processor 123 is actuated, to relate the coordinate system of the preoperative CT images, to that of the fluoroscope images, preferably by means of image feature comparison. Finally, the disc insertion position determined in the spine model generator is implanted onto the fluoroscope images displayed on the fluoroscope display unit 124, such that the surgeon can compare the actual disc position with the intended disc position on screen. The whole process and the computing steps are overseen by means of the system computer 120.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A system for intraoperatively placing an artificial disc at a predetermined position between two vertebrae of a subject, said system comprising:

a computing system having a storage medium including a set of preoperative CT data showing said two vertebrae and said predetermined position of said disc between them;

at least one three-dimensional target having radio-opaque markers adapted to be attached to at least one of said vertebrae to define the position of said vertebra in at least one intra-operative fluoroscope image of the subject;

a tool for intra-operative insertion of said artificial disc; and a registration system for relating said at least one intra-operative fluoroscope image to said set of preoperative CT data, such that said predetermined disc position is displayed in said at least one fluoroscope image of the subject, thereby enabling intraoperative placement of said artificial disc in said predetermined disc position.

2. A system according to claim 1 and wherein said predetermined position of said disc is obtained from predefined geometrical information about the position.

3. A system according to claim 1 and wherein said predetermined position of said disc is obtained by adjusting said disc position in a model obtained from said preoperative CT data, such that facet joints between said vertebrae are in minimally stressed positions.

4. A system according to claim 1 and further comprising at least two pins attached to each of said vertebrae, each of said pins comprising at least two radio-opaque markers disposed at known positions along said pins, such that said pins define the three-dimensional position of said vertebrae in said fluoroscope images of the subject, such that said target may be removed to allow intra-operative placement of said disc in said predetermined position.

5. A system according to claim 1 and further comprising at least one pin attached to each of said vertebra, each of said pins comprising at least three radio-opaque markers disposed at fixed positions along said pins, such that said pins define the three-dimensional position of said vertebrae in said fluoroscope images of the subject, such that said target may be removed to allow intra-operative placement of said disc in said predetermined position.

6. A system according to claim 1 and wherein said insertion tool is either a manually operated tool or a robotically operated tool.

7. A system according to claim 1, wherein said at least one three-dimensional target comprises at least two pins attached to one of said two vertebrae, each of said at least two pins comprising at least two radio-opaque markers disposed along their length, such that the position of said vertebra is defined in at least one intra-operative fluoroscope image of the subject.

8. A method of intraoperative positioning an artificial disc between two vertebrae of a subject, said method comprising the steps of:

generating from a preoperative set of CT data, a CT model showing said vertebrae;

predetermining a position for said disc between said vertebrae, and defining said position in said model;

attaching at least one three-dimensional target to one of said vertebrae;

generating at least one fluoroscope image of the subject, such that the three-dimensional position of said one of said vertebrae is defined in said at least one fluoroscope image by means of said at least one target;

registering said at least one fluoroscope image of the subject with said CT model, such that a rendering of said disc in its predetermined position is shown on said at least one fluoroscope image; and using said at least one fluoroscope image to position said disc intra-operatively such that it can be disposed in said predetermined disc position.

9. A method according to claim 8 and wherein said artificial disc is disposed in said predetermined disc position by ensuring that said intra-operative position in said fluoroscope image essentially coincides with said display of said predetermined disc position.

10. A method according to claim 8 and wherein said predetermined disc position is obtained from predefined geometrical information about the optimum position.

11. A method according to claim 8 and wherein said predetermined disc position is obtained by adjusting said disc position in said CT model such that facet joints between said vertebrae are in minimally stressed positions.

12. A method according to claim 8 and further comprising the steps of:
   providing at least four pins, each of said pins comprising at least two radio-opaque markers disposed at known positions along their length;
   attaching at least two of said pins to each of said vertebrae, such that said pins define the three-dimensional position of said vertebrae in said at least one fluoroscope image;
   utilizing the relationship between said known positions of said target and said pins to compute a transformation between the position of said target and said pins; and
   removing said target to facilitate access to said vertebrae.

13. A method according to claim 8 and further comprising the steps of:
   providing at least two pins, each of said pins comprising at least three radio-opaque markers disposed at known positions along said pins;
   attaching at least one of said pins to each of said vertebrae, such that said pins define the three-dimensional position of said vertebrae in said at least one fluoroscope image;
   utilizing the relationship between said known positions of said target and said pins to compute a transformation between the position of said target and said pins; and
   removing said target to facilitate access to said vertebrae.

14. A system for intraoperative placing an artificial disc at a predetermined position between two vertebrae of a subject, said system comprising:
   a computing system having a storage medium including a set of preoperative CT data showing said two vertebrae and said predetermined position of said disc between them;
   at least one three-dimensional target having radio-opaque markers adapted to be attached to at least one of said vertebrae to define the position of said vertebra in at least one intra-operative fluoroscope image of the subject;
   a jig adapted to be attached to at least one of said vertebrae and supporting a reproducibly alignable pointer; and
   a registration system for relating said at least one intra-operative fluoroscope image to said set of preoperative CT data, such that said predetermined disc position and said pointer are displayed in said at least one fluoroscope image of the subject, thereby enabling use of said pointer for intraoperative placement of said artificial disc in its predetermined position without the need to view a fluoroscope image.

15. A system for intraoperatively inserting a surgical tool into a predetermined position at a surgical site of a subject, said system comprising:
   a computing system having a storage medium including a set of preoperative CT data showing said surgical site and said predetermined position of said surgical tool;
   at least one three-dimensional target having radio-opaque markers adapted to be attached to a feature of said subject at said surgical site to define the position of said feature in at least one intra-operative fluoroscope image of the subject; and
   a system for registering said at least one intra-operative fluoroscope image to said set of preoperative CT data, such that said predetermined position of said surgical tool is displayed in at least one fluoroscope image of the subject, thereby enabling intraoperative insertion of said surgical tool into said predetermined position.

16. A system for intraoperatively placing an artificial disc at a predetermined position between two vertebrae of a subject, said system comprising:
   a computing system having a storage medium including a set of preoperative CT data showing said two vertebrae and said predetermined position of said disc between them;
   a tool for intra-operative insertion of said artificial disc;
   a registration system for relating said at least one intra-operative fluoroscope image to said set of preoperative CT data, such that said predetermined disc position is displayed in said at least one fluoroscope image of the subject, thereby enabling intraoperative placement of said artificial disc in said predetermined disc position; and
   a set of pins for attaching to said two vertebrae, said pins comprising a plurality of radio-opaque markers disposed along their lengths, such that said pins define the three-dimensional position of said two vertebrae in said fluoroscope images of the subject.

17. A system according to claim 16 wherein said set of pins for attaching to said two vertebrae comprises either of:
   at least two pins attached to each of said two vertebrae, each of said at least two pins comprising at least two radio-opaque markers disposed along their length, or
   at least one pin attached to each of said two vertebra, each of said at least one pin comprising at least three radio-opaque markers disposed at known positions along its length.

18. A system according to claim 16 wherein said predetermined position of said disc is obtained from predefined geometrical information about the position.

19. A system according to claim 16 wherein said predetermined position of said disc is obtained by adjusting said disc position in a model obtained from said preoperative CT data, such that facet joints between said vertebrae are in minimally stressed positions.

20. A system according to claim 16 wherein said set of pins for attaching to said two vertebrae comprises at least one pin attached to each of said two vertebra, said at least one pin being devoid of protruding radio-opaque markers, and having a known orientation and thickness, such that said pins define the three-dimensional position of said two vertebrae in said fluoroscope images of the subject.

21. A system according to claim 16 wherein said set of pins for attaching to said two vertebrae comprises at least one pin attached to each of said two vertebra, said at least one pin being devoid of protruding radio-opaque markers, and having a known orientation and shape, such that said pins define the three-dimensional position of said two vertebrae in said fluoroscope images of the subject.

22. A system according to claim 16 wherein said set of pins for attaching to said two vertebrae comprises at least 3 pins attached to each of said two vertebrae, each of said pins comprising one radio-opaque marker disposed along its length.

23. A method of intraoperative positioning an artificial disc between two vertebrae of a subject, said method comprising the steps of:
- generating from a preoperative set of CT data, a CT model showing said vertebrae;
- predetermining a position for said disc between said vertebrae, and defining said position in said model;
- attaching a set of pins to said two vertebrae, said pins comprising a plurality of radio-opaque markers disposed along their length;
- generating at least one fluoroscope image of the subject, including at least part of said two vertebrae and said pins, such that the three-dimensional positions of said vertebrae are defined in said at least one fluoroscope image by means of said pins;
- registering said at least one fluoroscope image of the subject with said CT model, such that a rendering of said disc in its predetermined position is shown on said at least one fluoroscope image; and
- using said at least one fluoroscope image to position said disc intra-operatively such that it can be disposed in said predetermined disc position.

24. A method according to claim 23, wherein said set of pins attached to said two vertebrae comprises either of:
- at least two pins attached to each of said two vertebrae, each of said at least two pins comprising at least two radio-opaque markers disposed along their length, or
- at least one pin attached to each of said two vertebra, each of said at least one pin comprising at least three radio-opaque markers disposed at known positions along its length.

25. A method according to claim 23 and wherein said artificial disc is disposed in said predetermined disc position by ensuring that said intra-operative position in said fluoroscope image essentially coincides with said display of said predetermined disc position.

26. A method according to claim 23 and wherein said predetermined disc position is obtained from predefined geometrical information about the optimum position.

27. A method according to claim 23 and wherein said predetermined disc position is obtained by adjusting said disc position in said CT model such that facet joints between said vertebrae are in minimally stressed positions.

* * * * *